United States Patent [19]
Wahlstrand et al.

[11] Patent Number: 5,534,018
[45] Date of Patent: Jul. 9, 1996

[54] AUTOMATIC LEAD RECOGNITION FOR IMPLANTABLE MEDICAL DEVICE

[75] Inventors: John D. Wahlstrand, Shoreview; Daniel J. Baxter, St. Paul; R. Michael Ecker, Anoka; Daniel R. Greeninger, Coon Rapids; Charles G. Yerich, Fridley, all of Minn.

[73] Assignee: Medtronic, Inc., Minneapolis, Minn.

[21] Appl. No.: 346,661

[22] Filed: Nov. 30, 1994

[51] Int. Cl.$^6$ .............................. A61N 1/00; A61N 1/362
[52] U.S. Cl. ................... 607/27; 607/28; 607/9; 607/29
[58] Field of Search ................... 607/9, 27, 28, 607/29; 128/734

[56] References Cited

U.S. PATENT DOCUMENTS

| | | | |
|---|---|---|---|
| 3,965,418 | 6/1976 | Bauer et al. | 324/99 D |
| 4,250,884 | 2/1981 | Hartlaub et al. . | |
| 4,290,430 | 9/1981 | Bihn et al. | 607/27 |
| 4,374,382 | 2/1983 | Markowitz . | |
| 4,476,868 | 10/1984 | Thompson . | |
| 4,556,063 | 12/1985 | Thompson et al. . | |
| 4,790,318 | 12/1988 | Elmqvist et al. . | |
| 4,805,621 | 2/1989 | Heinze et al. . | |
| 4,901,725 | 2/1990 | Nappholz et al. . | |
| 4,951,682 | 8/1990 | Petre | 128/734 |
| 4,964,407 | 10/1990 | Baker, Jr. et al. . | |
| 5,003,975 | 4/1991 | Nefalfinger et al. . | |
| 5,052,388 | 10/1991 | Sivula et al. . | |
| 5,127,404 | 7/1992 | Wyborny et al. . | |
| 5,201,808 | 4/1993 | Steinhaus et al. . | |
| 5,318,593 | 6/1994 | Duggan . | |
| 5,413,593 | 5/1995 | Spinelli et al. | 607/27 |

FOREIGN PATENT DOCUMENTS

| | | | |
|---|---|---|---|
| 0338363 | 10/1989 | European Pat. Off. | 607/28 |
| 0338364 | 10/1989 | European Pat. Off. | 607/28 |

*Primary Examiner*—Angela D. Sykes
*Assistant Examiner*—Stephen Huang
*Attorney, Agent, or Firm*—Michael B. Atlass; Harold R. Patton

[57] ABSTRACT

A method and apparatus for determining the availability of unipolar and/or bipolar pacing/sensing paths in a body-implantable cardiac pacing system. In one embodiment, a pacemaker system includes impedance monitoring circuitry for periodically measuring impedance between pairs of electrodes that are potentially available for pacing and/or sensing. This impedance monitoring circuitry includes circuitry for delivering excitation pulses between pairs of potentially available electrodes (including the pacemaker canister in the case of unipolar pacing or sensing), and for monitoring the current and voltage between those pairs of electrodes during delivery of an excitation pulse. Availability of a pair of electrodes for pacing and/or sensing is indicated if the impedance between a pair of electrodes is found to lie within a predetermined range. Detection of availability of a particular pair of electrodes is used initially as an indication that the pacing system has been implanted, and is also used to distinguish between unipolar and bipolar leads in the pacing system.

2 Claims, 4 Drawing Sheets

AUTOMATIC LEAD RECOGNITION FOR IMPLANTABLE MEDICAL DEVICE

FIELD OF THE INVENTION

This invention relates generally to the field of automatic, body-implantable medical device systems, and more particularly to implantable device systems including one or more electrically conductive leads.

BACKGROUND OF THE INVENTION

A wide assortment of automatic, body-implantable medical devices are presently known and commercially available. The class of such devices includes cardiac pacemakers, cardiac defibrillators and cardioverters, neural stimulators and many others.

In general, cardiac pacemakers are electrical devices used to supplant some or all of an abnormal heart's natural pacing function. Pacemakers typically operate to deliver appropriately timed electrical stimulation signals, sometimes called pacing pulses, designed to cause the myocardium to contract or "beat."

Known and commercially available pacemakers are typically characterized according the chambers of the heart to which they are capable of delivering stimuli, and their responses, if any, to sensed intrinsic electrical cardiac activity. Some pacemakers, especially early ones, deliver pacing stimuli at fixed, regular intervals without regard to naturally occurring cardiac activity. More commonly at present, however, pacemakers sense electrical cardiac activity in one or both chambers of the heart, and inhibit or trigger delivery of pacing stimuli to the heart based upon the occurrence and recognition of such sensed intrinsic electrical events.

The Inter-Society Commission for Heart Diseases has established a standard three-letter descriptive code to characterize pacemakers. The first letter of the ICHD code indicates which chambers of the heart the pacemaker is capable of pacing (atrial (A), ventricular (V), or atrial and ventricular (D)). The second letter indicates which chambers of the heart the pacemaker is capable of sensing (A, V, or D), and the third letter indicates the response of the pacemaker to a sensed intrinsic event (triggered (T), inhibited (I), or dual (D)).

A VVI pacemaker, for example, senses electrical cardiac activity only in the ventricle of a patients heart, and delivers pacing stimuli only in the absence of sensed electrical signals indicative of natural ventricular contractions (an "inhibited" response). A DDD pacemaker, on the other hand, senses electrical activity in both the atrium and ventricle of the heart (an "inhibited" response), and delivers atrial pacing stimuli only in the absence of sensed signals indicative of natural atrial contractions, and ventricular stimuli only in the absence of sensed signals indicative of natural ventricular contractions (an "inhibited" response). The delivery of each stimulus by a DDD pacemaker is synchronized with prior sensed or paced events (a "triggered" response, and since the responses are also "inhibited" as noted above, the third letter in the ICHD code is "D").

Many state-of-the-art pacemakers are capable of performing either unipolar or bipolar sensing and of pacing in either chamber of the heart. Unipolar pacing requires an elongate lead having only one insulated conductor therein and only one generally distal electrode disposed thereon. As will be appreciated by those of ordinary skill in the art, in most unipolar configurations, the protective canister of the implanted device is conductive and functions as an electrode in pacing or sensing. In particular, for unipolar pacing the current path for stimulating pulses extends from the pacemaker's pulse generator, along the lead to the exposed distal electrode, through the cardiac tissue, and back to the pacemaker via the conductive canister.

For bipolar pacing and/or sensing, on the other hand, a lead having two mutually isolated conductors and two electrodes disposed thereon is required. Typically, one electrode is disposed at the distal end of the lead and is referred to as the "tip" electrode, while the second electrode is spaced back somewhat from the distal end of the lead and is referred to as a "ring" electrode. The current path for bipolar pacing extends from the pulse generator in the pacemaker, along a first of the two lead conductors to the tip electrode, through the cardiac tissue to the ring electrode, and back to the pacemaker along the second of the two lead conductors.

Typically, a fully-featured DDD pacemaker, since it is capable of sensing and pacing in both chambers of the heart, can be programmed to operate in modes other than DDD, for example, VVD, VVI, AAI, etc .... In addition, many state-of-the-art pacemakers can be programmed to operate in either unipolar or bipolar pacing and sensing modes. This gives the implanting physician considerable flexibility in configuring a pacing system to suit the particular needs of a given patient. In addition, since most of today's pacemakers are non-invasively programmable post-implant, the physician or clinician can re-program the already implanted device to operate in different modes and with different pacing and sensing polarities in response to changes in the patient's needs and condition.

Many pacemakers can accept and will operate with either unipolar or bipolar leads. Thus, it is important for the physician to be aware of which type of leads are used in a given instance, since it would be inappropriate to program the device into a bipolar pacing and/or sensing mode when only unipolar leads have been implanted. Similarly, if one of the two conductors or electrodes on an implanted bipolar lead were to fail for some reason (e.g., breakage of a conductor due to metal fatigue, poor connections between the lead and the pacemaker itself, tissue degradation at the electrode site, subclavian crushing of the lead, metal ion oxidation, short of lead conductors due to urethane/silicon breakdown, etc...) it would be necessary to re-program the pacemaker into unipolar pacing and sensing modes in order for the pacemaker to function properly. The need for such re-programming due to lead failure or improper initial programming, however, would only become apparent upon careful examination of the patient in a clinical setting, which may not occur frequently enough to ensure proper operation of the pacemaker over a long term of implant.

SUMMARY OF THE INVENTION

In view of the foregoing, it is believed by the inventors that it would be advantageous to endow an implantable device such as a pacemaker with the ability to automatically and chronically distinguish between unipolar and bipolar leads coupled to it, and verify on an ongoing basis post-implant, the continued functionality of the leads.

Thus, the present invention is directed to a method and apparatus to be incorporated into an implantable device system for periodically performing a test to determine what type of pacing and sensing paths (i.e., unipolar or bipolar) are presently available to the device.

In one embodiment of the invention, an implantable pacemaker capable of both unipolar and bipolar pacing and sensing in one or both chambers of the heart uses subthreshold impedance measurements on all potentially available pace/sense paths (atrial unipolar and bipolar, ventricular unipolar and bipolar) to perform various lead recognition functions, including, in the preferred embodiment, automatic implant detection, automatic implant polarity configuration, automatic bipolar lead monitoring, and polarity programming confirmation.

In accordance with one aspect of the present invention, automatic implant detection can be performed such that upon attachment of leads to the pacemaker and implantation in a patient, the system automatically detects characteristics of impedance on the pace/sense paths and determines that implantation has occurred. Then, the pacemaker can be automatically initialized to begin performing post-implant functions, for example, diagnostic functions, rate response function initialization, and the like, without physician intervention.

In accordance with another aspect of the present invention, automatic polarity configuration is available allowing the pacemaker to self-adapt to desired polarity modes once the device ascertains what modes are available based upon the types of leads used in a particular application.

In accordance with yet another aspect of the invention, bipolar lead monitoring is carried out on a chronic, ongoing basis, such that lead failures, even intermittent ones or ones that occur long after implant, can be detected and responded to, thereby enhancing the efficacy and reliability of the system. This monitoring can be configured to be asynchronous, or synchronized to sensed and/or paced events.

In accordance with still another aspect of the invention, polarity programming confirmation is provided automatically upon initiation of a non-invasive programming session, such that improper programming of the device is prevented.

The various lead recognition functions achievable with the present invention each involve the delivery of sub-threshold voltage pulses on each of the potentially available pace/sense paths of the system, in order to make measurements of the impedance observed along each of those paths. (By sub-threshold, it is meant that the energy level of the pulses delivered for the purposes of measuring pace/sense path impedance is lower than the patients stimulation threshold energy levels that could evoke a cardiac response.) The impedance measurements are then assessed in relation to predetermined control values to determine whether each potential pace/sense path is actually available.

BRIEF DESCRIPTION OF THE DRAWINGS

The foregoing and other aspects of the present invention will perhaps be best understood with reference to a detailed description of a particular embodiment of the invention, when read in conjunction with the accompanying drawings, wherein.

Although the present invention will be described herein with reference to a specific embodiment of the invention, namely, a dual-chamber, unipolar- and bipolarcapable pacemaker, it is contemplated that the present invention may be advantageously practiced in connection with other types of body-implantable medical device systems having multiple conductive paths potentially available for the purposes of performing sensing of electrical signals or delivery of electrical signals. It is believed that adaptation of the present invention as described herein to such other applications would be readily accomplished by those of ordinary skill in the art having the benefit of this disclosure.

DETAILED DESCRIPTION OF A SPECIFIC EMBODIMENT OF THE INVENTION

Figure 1:
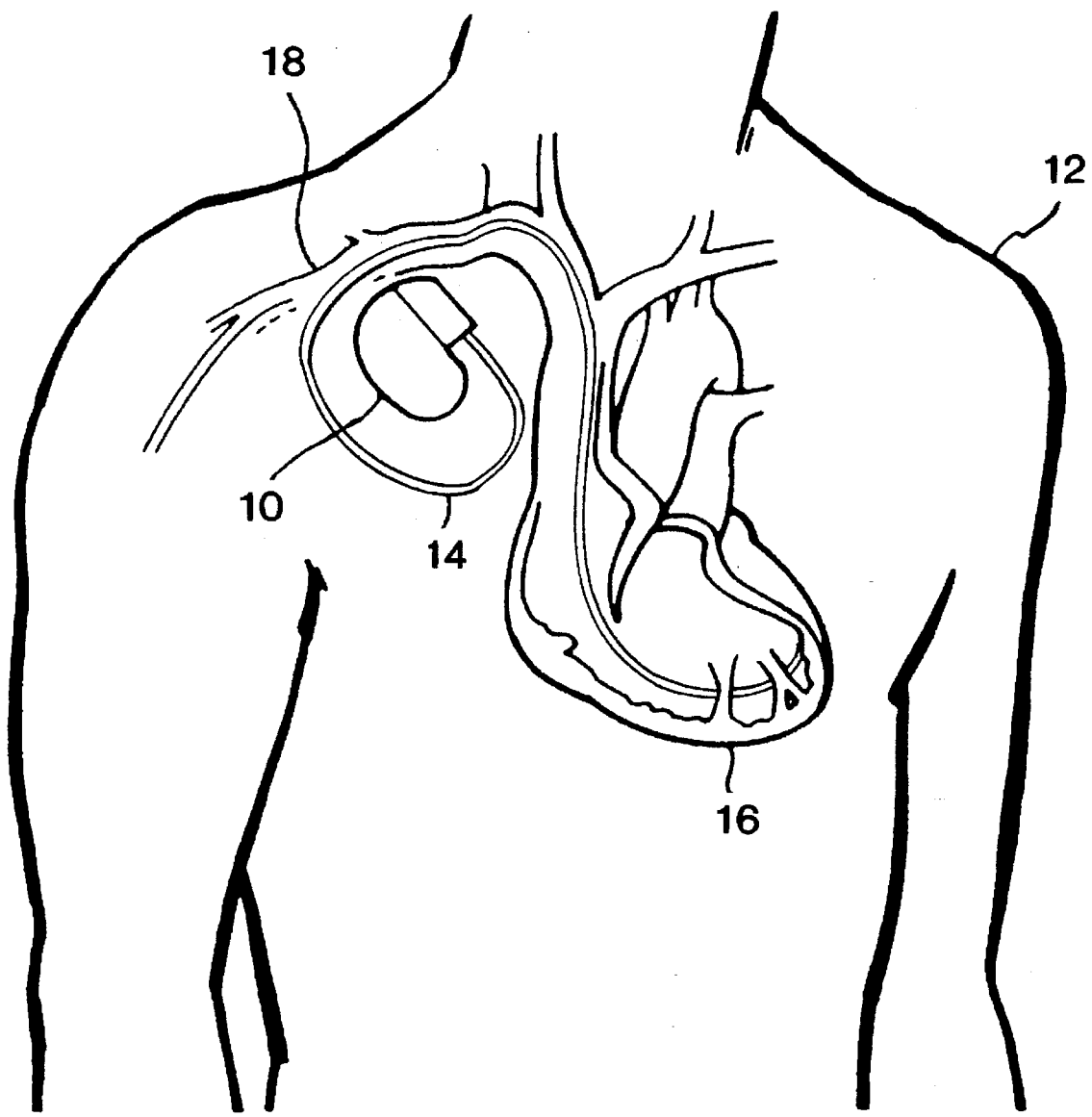
FIG. 1 is an illustration of a pacemaker in accordance with one aspect of the present invention having been implanted in a conventional manner into a patient.

Referring to FIG. 1, there is shown an illustration of generally where a pacemaker 10 in accordance with one embodiment of the invention may be implanted in a patient 12. In accordance with conventional practice in the art, pacemaker 10 is housed within a hermetically sealed, biologically inert outer canister, which may itself be conductive and thus serve as an indifferent electrode in the pacemaker's pacing/sensing circuit. One or more pacemaker leads, collectively identified with reference numeral 14 in FIG. 1 are electrically coupled to pacemaker 10 in a conventional manner, extending into the patient's heart 16 via a vein 18. Disposed generally near the distal end of lead 14 are one or more exposed conductive electrodes for receiving electrical cardiac signals and/or for delivering electrical pacing stimuli to heart 16. As will be appreciated by those of ordinary skill in the art, lead 14 may be implanted with its distal end situated in either the atrium or ventricle of heart 16.

Figure 2:
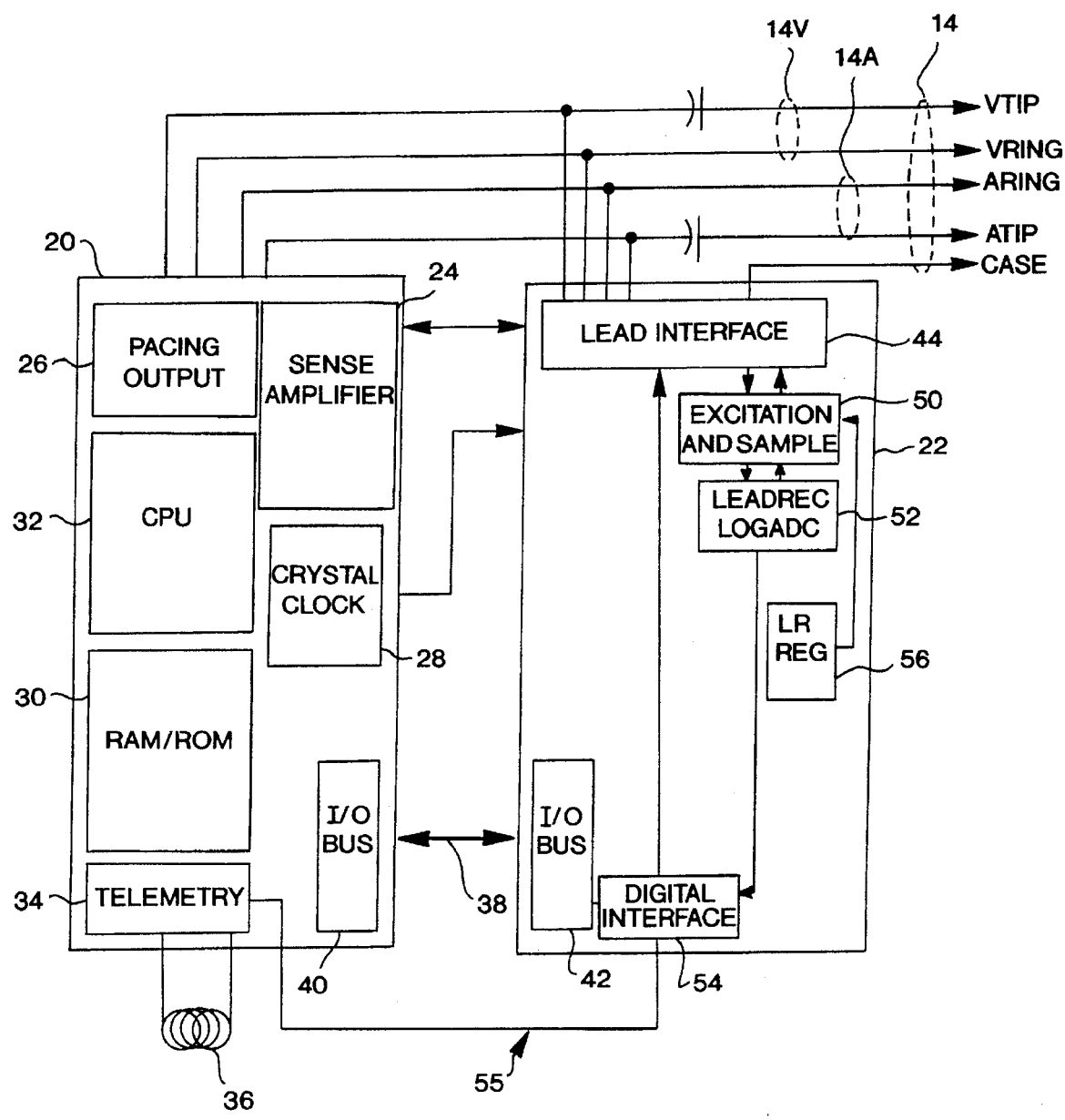
FIG. 2 is an block diagram of the pacemaker from FIG. 1.

Turning now to FIG. 2, there is shown a block diagram of the electronic circuitry which makes up pacemaker 10 in accordance with the presently disclosed embodiment of the invention. As can be seen from FIG. 2, pacemaker 10 comprises a primary pacing/control circuit 20 and, in accordance with an important aspect of the present invention, a lead recognition circuit 22. (It is contemplated by the inventors that the block designated lead recognition circuit 22 in FIG. 2 may in one implementation of the invention be associated with circuitry for performing other pacemaker-related functions. For example, in one embodiment of the invention, circuit 22 additionally comprises circuitry for supporting activity and/or minute ventilation sensing in a rate-responsive cardiac pacemaker. Such an arrangement is described in co-pending U.S. patent application by Yerich et al. for a "Method and Apparatus for Rate Responsive Cardiac Pacing", filed as of the date of the present application and which is hereby incorporated by reference herein in its entirety. For the purposes of the present invention, however, only the circuitry in block 22 associated with the pacemaker's automatic lead recognition function will be described.

Much of the circuitry associated with pacing control circuit 20 is of conventional design, in accordance, for example, with what is disclosed in U.S. Pat. No. 5,052,388 to Sivula et al, entitled "Method and Apparatus for Implementing Activity Sensing in a Pulse Generator." The Sivula et al. '388 patent is hereby incorporated by reference herein in its entirety. To the extent that certain components of pacemaker 10 are purely conventional in their design and operation, such components will not be described herein in detail, as it is believed that design and implementation of such components would be a matter of routine to those of ordinary skill in the art. For example, pacing/control circuit 20 in FIG. 2 includes sense amplifier circuitry 24, pacing output circuitry 26, a crystal clock 28, a random-access memory and read-only memory (RAM/ROM) unit 30, a central processing unit (CPU) 32, and a telemetry circuit 34, all of which are well-known in the art.

Pacemaker 10 preferably includes an internal telemetry circuit 34 so that it is capable of being programmed by means of external programmer/control unit 17 (not shown in FIG. 1 ). Programmers and telemetry systems suitable for use in the practice of the present invention have been well known for many years.

Known programmers typically communicate with an implanted device via a bidirectional radio-frequency telemetry link, so that the programmer can transmit control commands and operational parameter values to be received by the implanted device, and so that the implanted device can communicate diagnostic and operational data to the programmer. Programmers believed to be suitable for the purposes of practicing the present invention include the Model 9760 and Model 9790 Programmers, commercially-available from Medtronic, Inc., Minneapolis, Minn.

Various telemetry systems for providing the necessary communications channels between an external programming unit and an implanted device have been developed and are well-known in the art. Telemetry systems believed to be suitable for the purposes of practicing the present invention are disclosed, for example, in the following U.S. Patents: U.S. Pat. No. 5,127,404 to Wyborny et al. entitled "Telemetry Format for Implanted Medical Device"; U.S. Pat. No. 4,374,382 to Markowitz entitled "Marker Channel Telemetry System for a Medical Device"; and U.S. Pat. No. 4,556,063 to Thompson et al. entitled "Telemetry System for a Medical Device". The Wyborny et al. '404, Markowitz '382, and Thompson et al. '063 patents are commonly assigned to the assignee of the present invention, and are each hereby incorporated by reference herein in their respective entireties.

Typically, telemetry systems such as those described in the above-referenced patents are employed in conjunction with an external programming/processing unit. One programmer for non-invasively programming a cardiac pacemaker is described in the above-referenced Hartlaub et al. '884 patent.

Most commonly, telemetry systems for implantable medical devices employ a radio-frequency (RF) transmitter and receiver in the device, and a corresponding RF transmitter and receiver in the external programming unit. Within the implantable device, the transmitter and receiver utilize a wire coil as an antenna for receiving downlink telemetry signals and for radiating RF signals for uplink telemetry. The system is modelled as an air-core coupled transformer. An example of such a telemetry system is shown in the above-referenced Thompson et al. '063 patent.

In order to communicate digital data using RF telemetry, a digital encoding scheme such as is described in the above-reference Wyborny et al. '404 patent can be used. In particular, for downlink telemetry a pulse interval modulation scheme may be employed, wherein the external programmer transmits a series of short RF "bursts" or pulses in which the interval between successive pulses (e.g., the interval from the trailing edge of one pulse to the trailing edge of the next) is modulated according to the data to be transmitted. For example, a shorter interval may encodes a digital "0" bit while a longer interval encodes a digital "1" bit.

For uplink telemetry, a pulse position modulation scheme may be employed to encode uplink telemetry data. For pulse position modulation, a plurality of time slots are defined in a data frame, and the presence or absence of pulses transmitted during each time slot encodes the data. For example, a sixteen position data frame may be defined, wherein a pulse in one of the time slots represents a unique four bit portion of data.

As depicted in FIG. 1, programming units such as the above-referenced Medtronic Model 9760 and 9790 programmers typically interface with the implanted device through the use of a programming head or programming paddle, a handheld unit adapted to be placed on the patient's body over the implant site of the patient's implanted device. A magnet in the programming head effects reed switch closure in the implanted device to initiate a telemetry session. Thereafter, uplink and downlink communication takes place between the implanted device's transmitter and receiver and a receiver and transmitter disposed within the programming head.

With continued reference to FIG. 2, pacemaker 10 is coupled to leads 14 which, when implanted, extend transvenously between the implant site of pacemaker 10 and the patient's heart 16, as previously noted with reference to FIG. 1. For the sake of clarity, the connections between leads 14 and the various components of pacemaker 10 are not shown in FIG. 2, although it will be clear to those of ordinary skill in the art that, for example, leads 14 will necessarily be coupled, either directly or indirectly, to sense amplifier circuitry 24 and pacing output circuit 26, in accordance with common practice, such that cardiac electrical signals may be conveyed to sensing circuitry 24, and pacing pulses may be delivered to cardiac tissue, via leads 14.

In the presently disclosed embodiment, two bipolar leads are employed—an atrial lead 14A having atrial tip and ring electrodes (ATIP and ARING in FIG. 2), and a ventricular lead 14V having ventricular tip and ring electrodes (VTIP and VRING in FIG. 2). Those of ordinary skill in the art will appreciate that a separate, electrically insulated conductor extending along the length of leads 14A and 14V is associated with each of the electrodes ATIP, ARING, VTIP, and VRING. That is, electrical signals applied, for example, to the VRING electrode are conducted along lead 14V on a first conductor (wire), whereas signals applied to the VTIP electrode are conducted along a second, separate, conductor in lead 14V. In addition, as noted above, the conductive hermetic canister 11 of pacemaker 10 serves as an indifferent electrode (CASE in FIG. 2).

As previously noted, pace/control circuit 20 includes central processing unit 32 which may be an off-the-shelf programmable microprocessor or microcontroller, but in the presently preferred embodiment of the invention is a custom integrated circuit. Although specific connections between CPU 32 and other components of pace/control circuit 20 are not shown in FIG. 2, it will be apparent to those of ordinary skill in the art that CPU 32 functions to control the timed operation of pacing output circuit 26 and sense amplifier circuit 24 under control of programming stored in RAM/ROM unit 30. It is believed that those of ordinary skill in the art will be familiar with such an operative arrangement.

With continued reference to FIG. 2, crystal oscillator circuit 28, in the presently preferred embodiment a 32,768-Hz crystal controlled oscillator, provides main timing clock signals to pace/control circuit 20 and to lead recognition circuit 22.

It is to be understood that the various components of pacemaker 10 depicted in FIG. 2 are powered by means of a battery (not shown) which is contained within the hermetic enclosure 11 of pacemaker 10, in accordance with common practice in the art. For the sake of clarity in the Figures, the battery and the connections between it and the other components of pacemaker 10 are not shown.

Pacing output circuit 26, which functions to generate pacing stimuli under control of signals issued by CPU 32, may be, for example, of the type disclosed in U.S. Pat. No. 4,476,868 to Thompson, entitled "Body Stimulator Output Circuit," which patent is hereby incorporated by reference herein in its entirety. Again, however, it is believed that those of ordinary skill in the art could select from among many various types of prior art pacing output circuits which would be suitable for the purposes of practicing the present invention.

As shown in FIG. 2, pace/control circuit 20 is coupled to lead recognition circuit 22 by means of multiple signal lines, designated collectively as 38 in FIG. 2. An I/O interface 40 in pace/control circuit 20 and a corresponding I/O interface 42 in lead recognition circuit 22 function to coordinate the transmission of signals between the two units 20 and 22.

With continued reference to FIG. 2, lead recognition circuit 22 includes a lead interface circuit 44, which essentially functions as a multiplexer to selectively couple the lead conductors associated with the ATIP, ARING, VTIP, and VRING electrodes of leads 14A and 14V to the remaining components of lead recognition circuitry 22. In the preferred embodiment, the selection of particular conductors can accomplished by interface circuit 44 under control of control signals originating from pace/control circuit 20 and communicated to lead interface circuit 44 via lines 38.

Coupled to lead interface circuit 44 in lead recognition circuit 22 is an excitation and sample circuit 50 which, as will be hereinafter described in greater detail, functions to generate biphasic excitation pulses which are conveyed along leads 14A and/or 14V for the purposes of measuring impedance between various combinations of electrodes ATIP, ARING, VTIP, and VRING, as determined by the multiplexing function of lead interface circuit 44. In addition, excitation and sample circuit 50 performs a sampling function on electrical signals present on the conductors of leads 14A and 14V.

The sample values obtained by excitation and sample circuit 50 are provided to a logarithmic analog-to-digital converter ("logadc") circuit 52. As its name suggests, logadc circuit 52 performs a logarithmic analog-to-digital conversion function on the sample values obtained by sample and excitation circuit 50, resulting in the derivation of values corresponding to the current and voltage on the conductors of leads 14A and 14V. These values, in turn, are used to derive an impedance value reflecting the impedance associated with a given pacing path defined by the conductors of leads 14A and 14V. This impedance value is determined in a digital interface circuit 54 which also functions to coordinate the transfer of digital information between lead recognition circuit 22 and pace/control circuit 20 on lines 38.

Finally, an lead recognition voltage regulator ("lrreg") circuit 56 is provided to define a reference voltage used by excitation and sample circuit 50.

Figure 3:
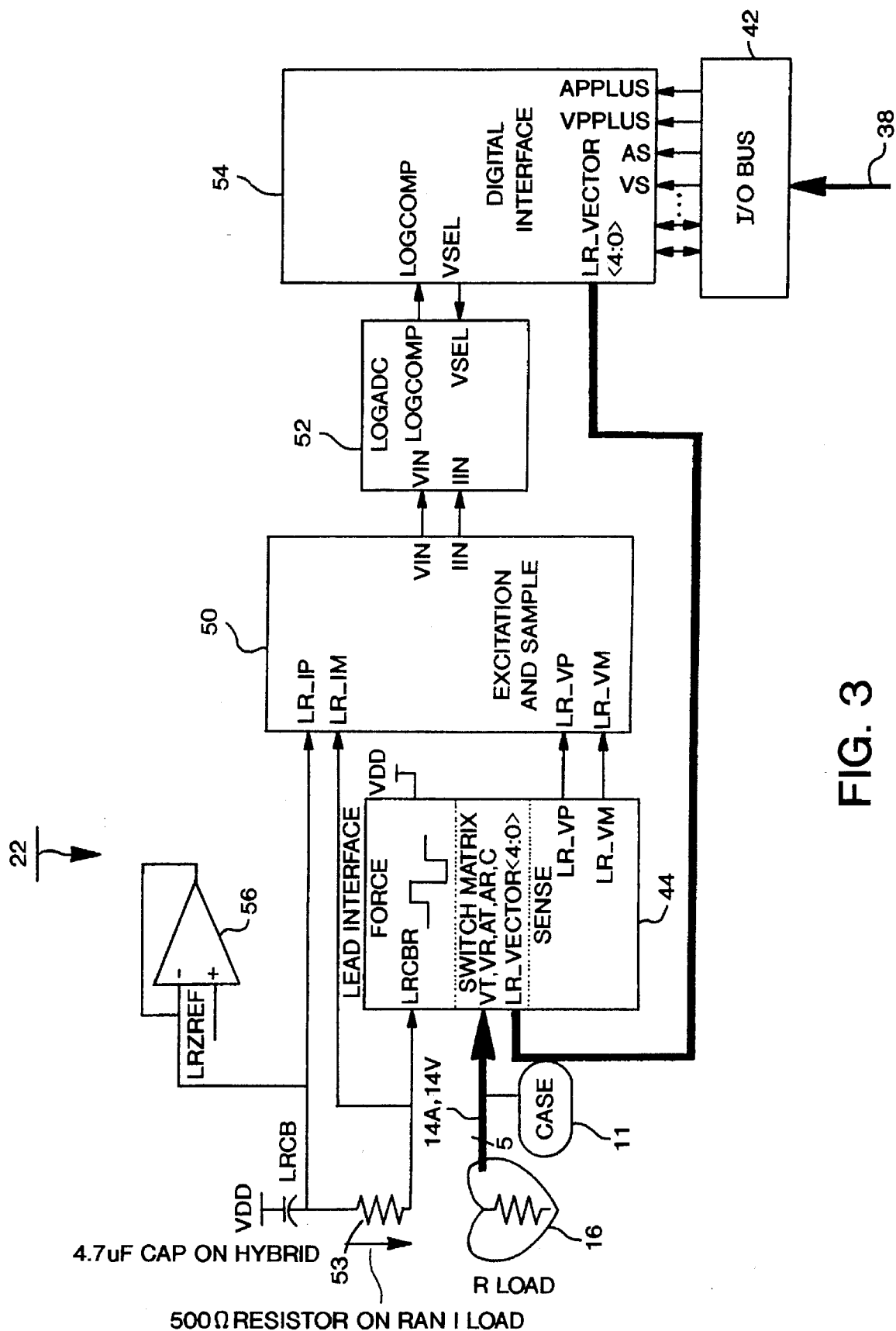
FIG. 3 is a block diagram of lead recognition circuitry incorporated into the pacemaker from FIG. 1.

Another block diagram of lead recognition circuit 22 in accordance with the presently disclosed embodiment of the invention is provided in FIG. 3. The block diagram of FIG. 3 is somewhat more detailed than that of FIG. 2, in that it shows more of the individual connections between components of lead recognition circuit 22.

As shown in FIG. 3, leads 14A and 14V extend between the patient's heart 16 and lead interface circuit 44. Since each lead 14A and 14V includes two separate internal conductors, leads 14A and 14V convey four separate electrical signals to lead interface circuit 44. Specifically, lead 14A conducts an atrial tip (AT) signal from its ATIP electrode and an atrial ring (AR) signal from its ARING electrode. Similarly, lead 14V conducts a ventricular tip (VT) signal and a ventricular ring (VR) signal from its VTIP and VRING electrodes, respectively. In addition, a signal C from the conductive case 11 of pacemaker 10, acting as an additional (fifth) electrode, is provided to interface circuit 44.

As will be familiar to those of ordinary skill in the art, the provision of two bipolar leads 14A and 14V, along with the use of the pacemaker's conductive canister as an additional electrode, allows a number of different pacing and sensing paths to be established in each chamber of the heart. In the atrial chamber, an atrial unipolar pacing/sensing path can be established wherein pacing pulses are delivered between one of the atrial tip electrode ATIP and the conductive canister (CAN) electrode. Alternatively, an atrial bipolar pacing/sensing path can be established, wherein pacing pulses are delivered between the ATIP and ARING electrodes of atrial lead 14A. Similarly, in the ventricular chamber, ventricular unipolar (VTIP-to-CASE) or bipolar (VTIP-to-VRING) pacing/sensing paths can be established.

Typically, and in the preferred embodiment, the pacing and sensing paths for each chamber of heart 16 are programmably selectable post-implant. Thus, although pacemaker 10 may be capable of operating in either unipolar or bipolar pacing modes in each chamber, the implanting physician may determine that unipolar pacing is preferred in view of the patient's particular condition, and can program pacemaker 10 accordingly. It is also common that a pacemaker, although operable in either unipolar or bipolar pacing/sensing modes, may be implanted with unipolar leads, thus making it impermissible for the pacemaker to be programmed into a bipolar mode.

As noted in the Summary of the Invention above, the present invention relates to a method and apparatus for automatically detecting when the pacemaker has been implanted in a patient, with either unipolar or bipolar leads, and further for automatically detecting what types of leads have been coupled to the pacemaker at implant. This is accomplished through delivery of sub-threshold biphasic voltage pulses on the possible pacing/sensing paths (atrial unipolar and bipolar, ventricular unipolar and bipolar), such that the impedances observed along those paths can be evaluated.

Figure 4:
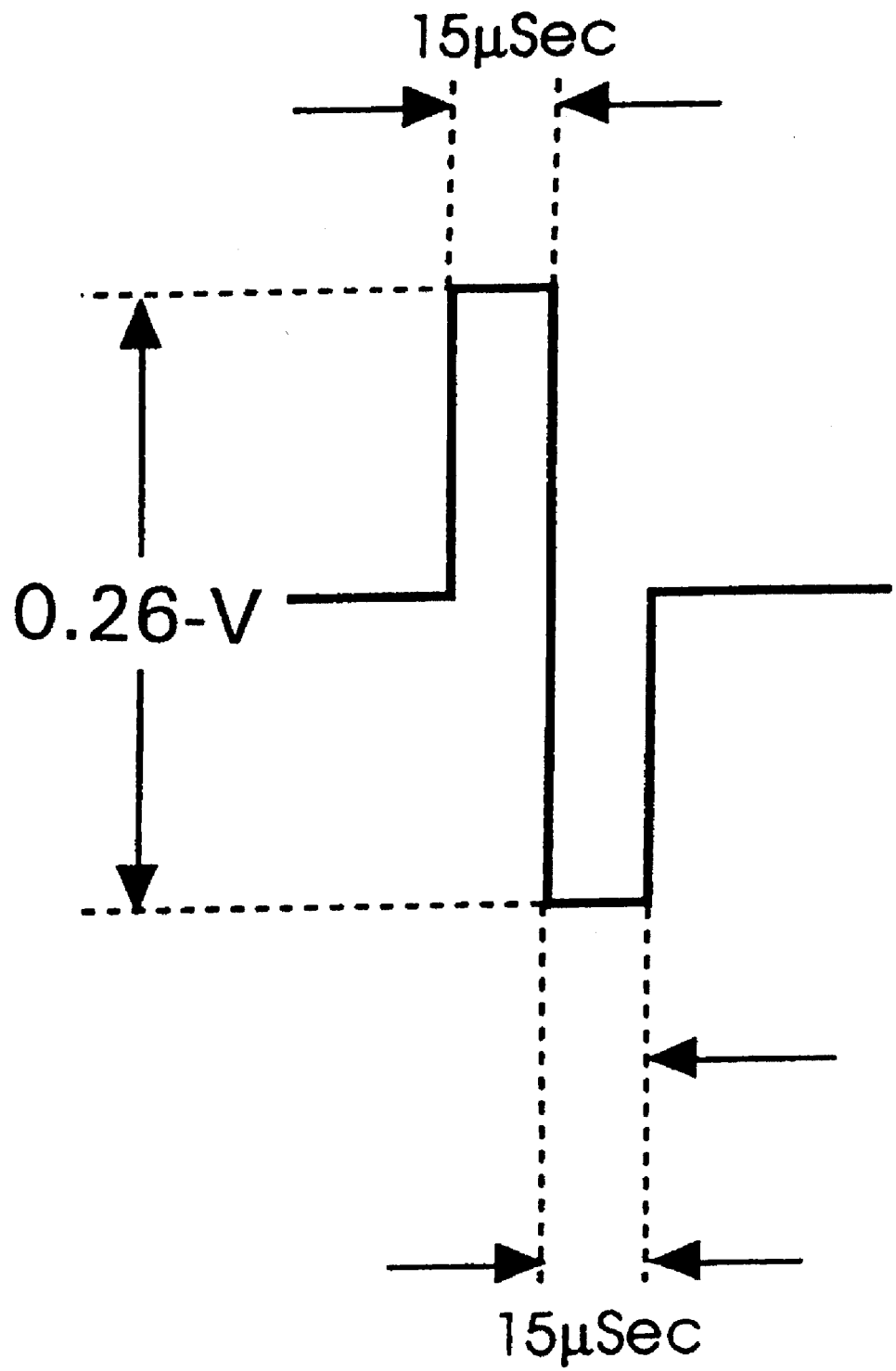
FIG. 4 is an illustration of the waveform of subthreshold pulses delivered by the lead recognition circuitry from FIG. 3 for the purpose of carrying out impedance measurement.

To this end, and with continued reference to FIG. 3, excitation and sample circuit 50 includes circuitry for generating the small sub-threshold biphasic voltage pulses, which, through lead interface circuit 44 are periodically and sequentially issued along each of the four possible pacing paths. An illustration of the biphasic pulse waveform generated by excitation and sample circuit 50 is shown in FIG. 4. As shown in FIG. 4, the biphasic pulses have 0.26-V peak-to-peak amplitudes, and last for 30-μSec (15-μSec each phase). The 0.26-V biphasic pulses are applied across the series combination of (1) a reference resistor, designated with reference numeral 53 in FIG. 3, and (2) the resistance through the lead conductors and heart. It is believed that the biphasic nature of the sub-threshold pulses offers the advantages over a monophasic pulse that the peak amplitude of each pulse is minimized given the overall energy content of the pulse, electrode polarization is canceled, and DC current is balanced to avoid longterm lead metal-ion oxidation. It is believed that the implementation of circuitry for generating pulses such as depicted in FIG. 4 would be a matter of routine engineering to those of ordinary skill in the art; therefore, the details of such circuitry will not be described further herein.

Returning to FIG. 3, lead interface circuit 44 functions in a multiplexer-like capacity during a lead recognition measurement circuit to direct a biphasic pulse from excitation and sample circuit 50 to each of the four pacing paths. Thus, during each measurement cycle, up to four excitation pulses are delivered. When a pulse is delivered along a given path, the resulting current and voltage are measured.

In the presently preferred embodiment of the invention, lead recognition measurement cycles can be triggered either synchronously or asynchronously with respect to the patient's cardiac function. Asynchronous measurement cycles occur once per second, while synchronous measurement cycles are initiated a predetermined time period following a paced or non-refractory sensed event in the chamber being measured. In the presently preferred embodiment, synchronous mode measurements are synchronized off of cardiac events (sensed and paced), so that the frequency and timing within the cardiac cycle of the measurements is related to the pacing and intrinsic rate. The predetermined delay period between detection of a sensed or paced cardiac event in a given cardiac chamber and delivery of sub-threshold pulse to that chamber may be among the programmably selectable parameters of pacemaker 10, in accordance with well-known practice in the art.

As noted above, when a sub-threshold biphasic pulse is delivered on a given path, the resultant voltage and current on that path are monitored. To this end, excitation and sample circuit 50 includes circuitry for obtaining samples of the voltage and current on the path being measured. In the presently preferred embodiment of the invention, the sampling rate is programmable, although the rate presently preferred is 1-Hz (i.e., one sample each second on each output/sensing path). For each measurement, the peak-to-peak voltage across the heart leads and the peak-to-peak voltage across reference resistor 53 are simultaneously sampled. Reference resistor 53 is configured in series with the heart so that the reference resistor's current is equal to that delivered to the heart. The voltage across reference resistor 53 is directly proportional to the current through the heart. After the sub-threshold pulse is delivered and the two resulting voltages are sampled, two multiple-cycle analog-to-digital conversions ensue. The conversions occur within logadc circuit 52 using the two sampled voltages available on the VIN and IIN lines. The VSEL control signal input to logadc circuit 52 selects between VIN and IIN. The result of each conversion appears at the LOGCOMP output as a serial bitstream.

For each sampling cycle of a given measurement cycle, digital interface circuit 54 produces two 7-bit digital values, VCODE and ICODE, from the serial bitstream provided by logadc circuit 52. The VCODE and ICODE values reflect the logarithm of the voltage sample VIN and the logarithm of the current sample IIN, respectively. These logarithmic values VCODE and ICODE are provided to digital interface circuit 54, where they are then subtracted, VCODE minus ICODE, to produce an impedance value (ZCODE).

ZCODE is a logarithmic value, and is related to impedance observed on the path being measured as follows:

LEAD IMPEDANCE (in ohms)=$500 \times (1+0.0741)^{ZCODE}$

The ICODE and VCODE values have an absolute range from zero to 127 (seven bits). More realistic values in actual use are in the range from zero to 45, corresponding to voltages of 10.4- to 259.4-mV and currents of 20.8- to 518.8-µA on the path being measured. The ZCODE value has an absolute range of $-127$ to $+127$ (eight bits), while the typical range is $-32$ to $+45$, corresponding to path impedances in the range from 50- to 12,500-Ω.

The ICODE and VCODE values derived during each sampling cycle of each measurement cycle are supplied via I/O lines 38 to pace/control circuit 20, where CPU 32 computes the corresponding ZCODE value. To support the lead recognition function in pacemaker 10, pace/control circuit 20 maintains a number of values in memory unit 30. Among these values are four path monitor values (a separate path monitor value is maintained for each of the four possible paths—atrial unipolar and bipolar, ventricular unipolar and bipolar). A path monitor status value is also maintained for each path, where the path monitor status value is an indicator of recent individual lead impedance measurements taken on the path to which it corresponds.

The resultant ZCODE value from each single path measurement is compared against two values, MINZ and MAXZ that correspond to normal lead impedances. If the measurement is greater than or equal to MINZ and less than or equal to MAXZ, the individual measurement is in-range; otherwise it is out-of-range.

Individual path monitor values in the path monitor registers are updated after both measurements for a given chamber have occurred during a measurement cycle. If both the bipolar path measurement and the unipolar path measurement for a given chamber are out-of-range, the updates for the two path monitors for that chamber are skipped. Otherwise, each path monitor uses the single measurement range result to update the individual path monitor status.

In the presently preferred embodiment, each path monitor register is a 32-bit shift register; also, associated with each path monitor register is an out-of-range counter. Updating of the path monitors occurs as follows: For each path monitor update, a bit is shifted into the path monitor shift register. The bit will be 0 if the measurement is in range, and 1 if the measurement is out-of-range. If the bit shifted in is a 1, the out-of-range counter is incremented. If the bit shifted out is a 1, the out-of-range counter is decremented.

The path monitor shift register and out-of-range counter for each path form an M-of-N monitor, where M is the number of measurements out of range over the last N measurements (N being the size in bits of the path monitor shift register).

For each measurement cycle, the status of the four path monitors is updated and evaluated. If the value of a path's out-of-range counter is equal to or greater than a predetermined (programmed) M value, the path monitor status register (which need be only 1-bit) is set to out-of-range; otherwise the path monitor status register is set to in-range. (In the presently preferred embodiment, initializing the path monitors involves setting all shift registers and out-of-range counters to contain all zeros, and setting all path monitor status bits to in-range.)

Path monitors are preferably frozen during any programming session, as evidenced by any valid programmer downlink. A measurement cycle in progress upon initiation of a programming session will be terminated and path monitor updates will not be made.

In the presently preferred embodiment of the invention, telemetry circuit 34 issues a signal on a line 55 (see FIG. 2) between telemetry circuit 34 and digital interface circuit 54 if RF signals are detected during a measurement cycle. The signal on line 55 tells interface circuit 54 to disregard the measurement values if RF is detected during the measurement cycle. This feature provides a desired level of immunity to RF downlink, since downlink RF bursts can induce energy on the lead system and confound the measurement.

The lead recognition feature of pacemaker 10 as thus far described may be advantageously utilized for several distinct functions: Implant Detection, Implant Polarity Configuration, Lead Monitoring, and Polarity Programming Confirmation. Implant Detection involves automatically recognizing when implant has occurred, and is beneficial for the purpose of initiating other processes in pacemaker 10, such as rate-response initialization and diagnostic data collection. Implant Polarity Configuration involves automatically configuring pacing and sensing polarities for each chamber based on the lead(s) implanted. Lead Monitoring entails monitoring each lead impedance value in each chamber, and comparing the results against programmable range and sensitivity criteria to determine lead status. If the criteria are met, the time and date are recorded. The Lead Monitor function may also involve automatically switching the pacing and sensing polarities from bipolar to unipolar (or vice versa) and/or providing a warning to a physician or clinician attempting to program the pacemaker to a bipolar pacing or sensing path when criteria for a viable bipolar path are not met.

Each of the above-described lead recognition functions can preferably be individually enabled and disabled. Implant Detection and Lead Monitoring are never active at the same time. Two time periods can be thought to exist: implant time, where Implant Detection is in progress and Implant Polarity Configuration can be either enabled or disabled, and chronic time, where Lead Monitoring and its various options may be either enabled or disabled by means of the programming system.

The Implant Detection function has two states: On and Off/Complete. During Implant Detection, lead recognition measurements are preferably made asynchronously and the path monitors will be updated to reflect path status. The Implant Detection function also preferably uses a count-down timer and the path monitor status registers to determine when implant has occurred. The count-down timer decrements once per second while the path monitors meet certain criteria, set forth below. If the criteria are not met, the timer resets itself to is maximum value.

The status of the path monitors are checked at the completion of each measurement cycle. The current path monitor status combination is compared to the path monitor status combination from the previous measurement cycle. If the current path monitor status combination is not one of the three listed below or is not the same as the previous path monitor status combination, the time is reset to its maximum value.

In the presently preferred dual-chamber embodiment of the invention, the three valid path monitor status combinations are as follows:

| 1. | Atrial Unipolar Path: | In-Range |
|---|---|---|
|  | Ventricular Unipolar Path: | In-Range |
|  | Atrial Bipolar Path: | In-Range |
|  | Ventricular Bipolar Path: | Out-Of-Range |
| 2. | Atrial Unipolar Path: | In-Range |
|  | Ventricular Unipolar Path: | In-Range |
|  | Atrial Bipolar Path: | Out-Of-Range |
|  | Ventricular Bipolar Path: | In-Range |
| 3. | Atrial Unipolar Path: | In-Range |
|  | Ventricular Unipolar Path: | In-Range |

-continued

| Atrial Bipolar Path: | In-Range |
|---|---|
| Ventricular Bipolar Path: | In-Range |

(The foregoing valid path monitor status combinations are specific to a particular bipolar pacemaker system. It is believed that those of ordinary skill in the art would comprehend that different combinations might be considered valid depending upon the particular pacing system with which the present invention is practiced.)

If Implant Detection is in progress and a programming session is initiated, the count-down timer is preferably frozen.

When the Implant Detection count-down timer reaches zero, the Implant Detection function terminates. At this time, if Implant Polarity Configuration is enabled, the bipolar path monitor status for each chamber is evaluated. If the bipolar path monitor status is in-range, the permanent pacing and sensing polarities for that chamber are set to or remain bipolar. If the bipolar path monitor status is out-of-range, the permanent pacing and sensing polarities for that chamber are set to or remain unipolar. The new polarities are put into effect at the start of the next pacing cycle.

Termination of the Implant Detection function can also cause the initiation of other pacemaker processes, as previously noted, including automatic initialization of rate-response function (which may involve accumulating patient data over a period of time before activation of rate-response operation—see the above-referenced U.S. patent application by Yerich et al.

If the Lead Monitor function is enabled, termination of the Implant Detection function also preferably causes reinitialization of all path monitors to in-range, loading of all path monitor shift registers with zeroes, and setting of all path monitor out-of-range counters to zero. If the Lead Monitor function is not enabled, all path monitors are frozen.

The Implant Detection function can be forced to complete via a command transmitted downlink from the external programmer. Likewise, the programmer can restart Implant Detection.

The Implant Polarity Configuration feature automatically sets pacing and sensing polarities individually for each chamber. Implant Polarity Configuration can be operational only while Implant Detection is in progress, and can be individually programmed On or Off. Implant Polarity Configuration uses the individual measurement cycle results acquired while Implant Detection is in progress, and each chamber is evaluated individually.

For Implant Polarity Configuration, if the most recent chamber bipolar measurement is in-range, the permanent pacing and sensing polarities are set to or remain bipolar. If the most recent chamber bipolar path is out-of-range, the permanent pacing and sensing polarities are set to or remain unipolar. The new polarities are put into effect at the start of the next pacing cycle. The pacing and sensing polarity decision is made with each measurement cycle.

The Lead Monitor function can be programmed to either "On", "On plus atrial polarity switch", "On plus ventricular polarity switch", or "On plus ventricular and atrial polarity switch." When Lead Monitor is active, the monitor trip criteria for each chamber are evaluated separately at the end of each cycle following completion of path monitor status updates. If the atrial path monitor changes from in-range to out-of-range and the atrial pace and sense polarities are not both unipolar, the atrial trip criteria are met. Similarly, if the ventricular path monitor changes from in-range to out-of-range and the ventricular pace and sense polarities are not both unipolar, the ventricular trip criteria are met.

When a given chamber's trip criteria is met, as set forth above, the following actions are taken:

1. A "trip-bit" maintained in memory by the pace/control circuitry 20 is set and a timestamp is recorded.
2. If the chamber polarity switch bit is set (i.e., if Bipolar Lead Monitor is enabled to "On plus atrial and/or ventricular polarity switch," as described above), the permanent pace and sense polarity will be set to unipolar for that chamber, starting at the beginning of the next pacing cycle.

An additional function of pacemaker 10 in connection with its lead recognition capability is Polarity Programming Confirmation, which may be enabled or disabled independently from the Implant Detect and Lead Monitor functions. At the start of a programming session, a single asynchronous lead recognition measurement cycle is initiated. At the completion of the measurement cycle, the ICODE and VCODE from that cycle are stored in a reserved memory location maintained by pacing/control circuit 20. These measured values are not used by the path monitors. The programmer can then interrogate pacemaker 10 and use the stored ICODE and VCODE to verify that a chamber's bipolar path is in-range before allowing the programmer to request pacing or sensing bipolarity for a given chamber.

(In an alternative implementation of the Polarity Programming Confirmation function, the most recent measurement results can be used as the Polarity Programming Confirmation data, combined with Path Monitor status to determine bipolar availability.)

Still another embodiment of the invention contemplated by the inventors involves operation of the lead recognition functions synchronously with the device's pacing and/or sensing functions. In this embodiment, lead recognition excitation pulses are delivered after a predetermined delay interval following paced and/or sensed events. The predetermined delay may be swept through its available range (determined by hardware) to detect lead fractures or shorts which might not be discernable with a fixed delay interval. This may be desirable because the effects of such fractures or shorts may be more or less discernable depending upon the amount of flex to the lead, which in turn is dependent upon cardiac activity.

In one embodiment of the invention contemplated by the inventors, lead recognition markers can be incorporated into the marker channel uplink (see the above-referenced Markowitz '382 patent).

From the foregoing detailed description of a specific embodiment of the invention, it should be apparent that a method and apparatus for providing a body-implantable medical device with the capability of recognizing the presence or absence of conductive leads coupled thereto through impedance measurement has been disclosed, and further that applications of this capability to provide such automatic implant detection, automatic implant polarity configuration, automatic and chronic bipolar lead monitoring, and polarity programming confirmation have been disclosed.

What is claimed is:

1. A body-implantable cardiac pacemaker system, comprising:
   an electronic circuit, wherein said electronic circuit comprises:
      an excitation circuit coupled to at least one conductor, for applying a sub-threshold symmetrical and bi-phasic voltage pulse along a current path;
      an impedance measurement circuit, coupled to said at least one conductor and to a second electrode, adapted to measure impedance along said current path during application of said sub-threshold voltage pulse;
      a comparison circuit, coupled to said impedance measurement circuit and adapted to determine whether said measured impedance lies within a predetermined impedance range, indicating availability of said current path for cardiac pacing;
   a hermetic enclosure for housing said electronic circuit;
   a flexible, elongate pacing/sensing lead having at least one conductor therein extending between proximal and distal ends of said lead, said at least one conductor being coupled at said proximal end to said electronic circuit in said hermetic enclosure and coupled near said distal end to a first conductive electrode adapted to be disposed in electrical contact with patient's cardiac tissue;
   a second electrode, electrically coupled to said electronic circuit in said hermetic enclosure, such that said current path is established extending from said electronic circuit, along said at least one lead to said electrode, through a portion of said patient's body tissue to said second electrode and back to said electronic circuit;
   Wherein said impedance measurement circuit further comprises:
      a sampling circuit for obtaining a sample of voltage between said first and second electrodes during said application of said excitation pulse and for obtaining a sample of current between said first and second electrodes during said application of said excitation pulse;
      an analog-to-digital converter for deriving a digital voltage value corresponding to a logarithm of said sampled voltage and a digital current value corresponding to the logarithm of said sampled current; and
      an impedance computation circuit for deriving from said digital voltage and current values a digital impedance value corresponding to the logarithm of the impedance between said first and second electrodes during application of said excitation pulse, wherein said voltage pulse is bi-phasic and on the order of 0.26 volts, peak to peak.

2. A body implantable cardiac pacemaker system for implantation into a patient's body:
   a hermetic enclosure for housing electronic circuitry;
   a flexible, elongate pacing/sensing lead having at least one conductor therein extending between proximal and distal ends of said lead, said at least one conductor being coupled at said proximal end to said electronic circuitry in said hermetic enclosure and coupled near to said distal end to a first conductive electrode adapted to be disposed in electrical contact with cardiac tissue in said patient's body;
   a second electrode, electrically coupled to said electronic circuitry in said hermetic enclosure, such that a current path is established extending from said electronic circuitry, along said at least one lead to said electrode, through a portion of said patient's body tissue to said second electrode and back to said electronic circuitry;
   said electronic circuitry comprising:
      an excitation circuit coupled to said at least one conductor, for applying a sub-threshold symmetrical and bi-phasic voltage pulse along said current path;
      an impedance measurement circuit, coupled to said at least one conductor and to said second electrode, adapted to measure impedance along said current path during application of said sub-threshold voltage pulse;

a comparison circuit, coupled to said impedance measurement circuit and adapted to determine whether said measured impedance lies within a predetermined impedance range, indicating availability of said current path for cardiac pacing;

wherein said voltage pulse is biphasic and on the order of 0.26 volts, peak to peak.

* * * * *